(12) United States Patent
Schroeder et al.

(10) Patent No.: US 7,199,285 B2
(45) Date of Patent: Apr. 3, 2007

(54) MODULATION OF ABSCISIC ACID SIGNAL TRANSDUCTION IN PLANTS

(75) Inventors: Julian Schroeder, La Jolla, CA (US); Veronique Hugouvieux, St. Egrève (FR); June M. Kwak, North Potomac, MD (US)

(73) Assignee: University of California, San Diego, La Jolla, CA (US)

( * ) Notice: Subject to any disclaimer, the term of this patent is extended or adjusted under 35 U.S.C. 154(b) by 437 days.

(21) Appl. No.: 10/740,084

(22) Filed: Dec. 18, 2003

(65) Prior Publication Data

US 2005/0193447 A1    Sep. 1, 2005

Related U.S. Application Data

(63) Continuation of application No. 09/882,986, filed on Jun. 14, 2001, now abandoned.

(60) Provisional application No. 60/212,068, filed on Jun. 14, 2000.

(51) Int. Cl.
*C12N 15/29* (2006.01)
*C12N 15/82* (2006.01)
*A01H 5/00* (2006.01)

(52) U.S. Cl. ............... 800/298; 800/278; 800/290; 800/287; 800/286; 800/294; 800/292; 800/293; 800/260

(58) Field of Classification Search ............. 800/278, 800/298, 286, 287, 260, 290, 294, 292, 293; 435/468
See application file for complete search history.

(56) References Cited

OTHER PUBLICATIONS

Colliver et al (1997, Plant Mol. Biol. 35:509-522).*
Emery et al (2003, Current Biology 13:1768-1774).*
"Accession No. NP_002477", *NCBI Database*.
"Accession No. P34160", *NCBI Database*.
Armstrong, F., et al., "Sensitivity to Abscisic of guard cell K+ channels is Suppressed by abi1-1, a mutant Arabidopsis gene encoding a putative protein phosphatase", *Proc. Natl. Acad. Sci U.S.A.*, 92. (1995),9520-9524.
Cutler, S., et al., "A Protein Farnesyl Tranferase Involved in Abscisic Acid Signal Transduction in Arabidopsis", *Science*, 273, (1996),1452-1455.
Koornneef, M., et al., "The Genetic and Molecular dissection of abscisic biosynthesis and signal transduction in Arabdipopsis", *Plant Physiol. Biochem*, 36, (1998),83-89.
Leung, J., et al., "Abscisic Acid Signal Transduction", *Annu. Rev. Plant Physiol. Plan. Mol. Biol.*, 49, (1998),199-222.
Leung, J., et al., "Arabidopsis ABA Response Gene AB11: Features of a Calcium-Modulated Protein Phosphatase", *Science*, 264, (1994), 1448-1452.
Li, J., et al., "Regulation of Abscisic Acid-Induced Stomatal Closure and Anion Channels by Guard Cell AAPK Kinase", *Science*, 287, (2000),300-303.
Macrobbie, E.A.C., "Signal Transduction and Ion Channels in Guard Cells", *Philos. Trans. R. Soc. Lond. B Biol. Sci.*, 353, (1998),1475-1488.
Meyer, K, et al., "A Protein Phosphatase 2C Involved in ABA Signal Transduction in *Arabidopsis thaliana*", *Science*, 287, (2000),300-303.
Pei, Z. M., et al., "Differential Abscisic Acid Regulation of Guard Cell Slow Anion Channels in Arabidopsis Wild-Type and abi1 anbi2 Mutants", *Plant Cell*, 9, (1997),409-423.
Pei, Z. M., et al., "Role of Farneyltransferase in ABA Regulation of Guard Cell Anion Channels and Plant Water Loss", *Science*, 282, (1998),287-290.
Ward, J. M., et al., "Roles of Ion Channels in Guard Cells", *Plant Cell*, 7, (1995),833-844.

* cited by examiner

*Primary Examiner*—Stuart F. Baum
(74) *Attorney, Agent, or Firm*—Schwegman, Lundberg, Woessner, & Kluth, P.A.

(57) ABSTRACT

The present invention provides methods of modulating abscisic acid signal transduction in plants. The method comprise introducing into the plant a recombinant expression cassette comprising a promoter operably linked to an ABH1 polynucleotide.

16 Claims, No Drawings

SEQUENCE LISTING

```
<160> NUMBER OF SEQ ID NOS: 4

<210> SEQ ID NO 1
<211> LENGTH: 2716
<212> TYPE: DNA
<213> ORGANISM: Arabidopsis thaliana
<220> FEATURE:
<221> NAME/KEY: CDS
<222> LOCATION: (37)..(2583)
<223> OTHER INFORMATION: abscisic acid (ABA) hypersensitive (ABH1) cDNA
<223> OTHER INFORMATION: ABH1 protein

<400> SEQUENCE: 1
aaagagacga actgaagaaa aacctctcgg aagaagatga gcaattggaa aactcttctc        60
cttcgcatcg gcgaaaaggg acctgagtac ggcacttcct ccgactacaa agaccacatc       120
gagacttgtt tcggtgtcat tcgtagagaa atcgagcgtt ctggagatca agttttgcct       180
tttctactac aatgtgctga acaattgcct cataagattc ctttgtatgg gactttgatt       240
ggtttgttga acttggagaa tgaagatttt gtccagaagc tagtagaaag tgtccacgct       300
aatttccagg tcgctttaga ttctggcaac tgcaacagta tccgtatatt gcttcgcttt       360
atgacttccc tgttgtgcag taaggttatt caacctgctt ctttgattgt cgtcttcgaa       420
acattgctat catctgctgc cactactgtg gatgaagaga aaggaaatcc atcatggcag       480
ccacaagctg acttttacgt tatatgcatc ttgtccagcc tcccgtgggg aggatcagaa       540
ctcgctgagc aagttcctga tgagattgaa agagtgttag ttgggataca agcttatttg       600
agcatccgaa agaattcttc cacctctggg ttaaactttt ttcacaacgg agaatttgaa       660
agcagccttg cagagaagga tttcgtggag gatctattgg atcgaattca gtctctggct       720
tccaatggat ggaaacttga aagcgtacct aggcctcatc tctcgtttga agctcaactc       780
gttgctggaa agtttcatga gctacgtccc attaaatgta tggaacaacc gagtccacct       840
tctgatcatt cgagggcata cagtggcaag caaaagcatg atgcattgac gagatatccc       900
cagagaattc gtaggttgaa tatatttcca gctaataaaa tggaggatgt acaaccaatt       960
gatcgttttg tcgtggagga gtatttgctg gatgtgctct tctatttgaa tggatgtcgg      1020
aaggagtgtg catcctacat ggctaatctt cctgttacat ttcggtacga gtatcttatg      1080
gcagagacac tattttctca gatactgctg ctaccccagc caccattcaa gactctttat      1140
tatacactcg tgattatgga tctttgtaag gctcttccgg gtgcctttcc tgctgttgtt      1200
gctggcgctg ttcgtgcact atttgagaaa atatccgact tagacatgga atccaggacg      1260
cgtcttatcc tctggttttc tcaccactta tccaacttcc aattcatctg gccgtgggaa      1320
gagtgggctt ttgtgttgga tcttcccaag tgggccccta agcgtgtatt tgttcaggag      1380
```

-continued

```
attttgcaaa gagaagtacg cttgtcttac tgggataaaa ttaagcagag cattgagaat    1440
gcgactgccc tagaagaatt acttcctcca aaagctggtc cgaattttat gtattccttg    1500
gaagaaggta aagagaaaac agaagaacag caattgtcag ccgaattgag caggaaggtc    1560
aaggaaaaac aaaccgcacg tgacatgata gtgtggattg aagaaacgat atatccagtt    1620
catggttttg aagttactct tacaatagtt gtacagacct tacttgacat cggatcaaaa    1680
agtttcactc atttggtcac tgtcctggag cgatatggcc aagtattttc aaagctttgt    1740
cctgataacg ataagcaggt gatgctatta tctcaagtga gtacatactg aaaaacaat     1800
gtacaaatga cggcggtggc aattgatagg atgatgggtt atagactagt atctaatcag    1860
gcaattgtta gatgggtgtt ctctccagaa aatgttgatc agtttcatgt gtctgatcag    1920
ccatgggaga tacttggcaa tgctcttaac aagacttata accgtatctc tgatttgagg    1980
aaagatatat caaacattac gaaaaatgtt ttggttgctg agaaagcttc agccaatgca    2040
cgagtagagt tggaggctgc tgagagcaaa ctttccctag tggaaggtga acccgttctt    2100
ggtgagaatc cagcgaagat gaagcgttta aaatcaacag tggagaagac aggggaagcg    2160
gagttatctc ttcgggagtc cctagaggca aaagaggctc ttcttaacag agctctctct    2220
gagaccgagg ttttactgct cttgctgttc caaagtttct taggtgtact gaaggaacgg    2280
ctcccagatc aactaaagt gagatcagtg caggatctaa aatctatagg tgctgaagat     2340
gacaagccat ctgcgatgga cgtggacagc gagaatggaa acccaaagaa gagttgcgaa    2400
gtcggtgaga gagaacagtg gtgcttatca acacttggct atctcacggc atttacaagg    2460
caatatgcga gcgagatatg gcctcacatg gagaagttgg agtcagaagt gttctcgggt    2520
gaagatgtgc atcctctctt tctccaagcc atatcttctg cacttcaatt cccattacat    2580
taatcttcct ctttcaatct caatcaaacc tgtctctttt gttttttgtt atgagattct    2640
gattctgaca tcaagttatt aggaaattga aagagtcaa aaaacaagag tttaaacttt     2700
aaaaaaaaaa aaaaaa                                                    2716
```

<210> SEQ ID NO 2
<211> LENGTH: 848
<212> TYPE: PRT
<213> ORGANISM: Arabidopsis thaliana
<220> FEATURE:
<223> OTHER INFORMATION: ABH1

<400> SEQUENCE: 2

```
Met Ser Asn Trp Lys Thr Leu Leu Arg Ile Gly Glu Lys Gly Pro
  1               5                  10                  15

Glu Tyr Gly Thr Ser Ser Asp Tyr Lys Asp His Ile Glu Thr Cys Phe
             20                  25                  30

Gly Val Ile Arg Arg Glu Ile Glu Arg Ser Gly Asp Gln Val Leu Pro
         35                  40                  45

Phe Leu Leu Gln Cys Ala Glu Gln Leu Pro His Lys Ile Pro Leu Tyr
     50                  55                  60

Gly Thr Leu Ile Gly Leu Leu Asn Leu Glu Asn Glu Asp Phe Val Gln
 65                  70                  75                  80

Lys Leu Val Glu Ser Val His Ala Asn Phe Gln Val Ala Leu Asp Ser
                 85                  90                  95

Gly Asn Cys Asn Ser Ile Arg Ile Leu Leu Arg Phe Met Thr Ser Leu
            100                 105                 110

Leu Cys Ser Lys Val Ile Gln Pro Ala Ser Leu Ile Val Val Phe Glu
```

```
            115                 120                 125
Thr Leu Leu Ser Ser Ala Ala Thr Thr Val Asp Glu Glu Lys Gly Asn
        130                 135                 140

Pro Ser Trp Gln Pro Gln Ala Asp Phe Tyr Val Ile Cys Ile Leu Ser
145                 150                 155                 160

Ser Leu Pro Trp Gly Gly Ser Glu Leu Ala Glu Gln Val Pro Asp Glu
                165                 170                 175

Ile Glu Arg Val Leu Val Gly Ile Gln Ala Tyr Leu Ser Ile Arg Lys
            180                 185                 190

Asn Ser Ser Thr Ser Gly Leu Asn Phe His Asn Gly Glu Phe Glu
        195                 200                 205

Ser Ser Leu Ala Glu Lys Asp Phe Val Glu Asp Leu Leu Asp Arg Ile
    210                 215                 220

Gln Ser Leu Ala Ser Asn Gly Trp Lys Leu Glu Ser Val Pro Arg Pro
225                 230                 235                 240

His Leu Ser Phe Glu Ala Gln Leu Val Ala Gly Lys Phe His Glu Leu
                245                 250                 255

Arg Pro Ile Lys Cys Met Glu Gln Pro Ser Pro Ser Asp His Ser
            260                 265                 270

Arg Ala Tyr Ser Gly Lys Gln Lys His Asp Ala Leu Thr Arg Tyr Pro
        275                 280                 285

Gln Arg Ile Arg Arg Leu Asn Ile Phe Pro Ala Asn Lys Met Glu Asp
    290                 295                 300

Val Gln Pro Ile Asp Arg Phe Val Val Glu Glu Tyr Leu Leu Asp Val
305                 310                 315                 320

Leu Phe Tyr Leu Asn Gly Cys Arg Lys Glu Cys Ala Ser Tyr Met Ala
                325                 330                 335

Asn Leu Pro Val Thr Phe Arg Tyr Glu Tyr Leu Met Ala Glu Thr Leu
            340                 345                 350

Phe Ser Gln Ile Leu Leu Pro Gln Pro Phe Lys Thr Leu Tyr
        355                 360                 365

Tyr Thr Leu Val Ile Met Asp Leu Cys Lys Ala Leu Pro Gly Ala Phe
    370                 375                 380

Pro Ala Val Val Ala Gly Ala Val Arg Ala Leu Phe Glu Lys Ile Ser
385                 390                 395                 400

Asp Leu Asp Met Glu Ser Arg Thr Arg Leu Ile Leu Trp Phe Ser His
                405                 410                 415

His Leu Ser Asn Phe Gln Phe Ile Trp Pro Trp Glu Gly Trp Ala Phe
            420                 425                 430

Val Leu Asp Leu Pro Lys Trp Ala Pro Lys Arg Val Phe Val Gln Glu
        435                 440                 445

Ile Leu Gln Arg Glu Val Arg Leu Ser Tyr Trp Asp Lys Ile Lys Gln
    450                 455                 460

Ser Ile Glu Asn Ala Thr Ala Leu Glu Glu Leu Leu Pro Pro Lys Ala
465                 470                 475                 480

Gly Pro Asn Phe Met Tyr Ser Leu Glu Glu Gly Lys Glu Lys Thr Glu
                485                 490                 495

Glu Gln Gln Leu Ser Ala Glu Leu Ser Arg Lys Val Lys Glu Lys Gln
            500                 505                 510

Thr Ala Arg Asp Met Ile Val Trp Ile Glu Glu Thr Ile Tyr Pro Val
        515                 520                 525

His Gly Phe Glu Val Thr Leu Thr Ile Val Val Gln Thr Leu Leu Asp
    530                 535                 540
```

```
Ile Gly Ser Lys Ser Phe Thr His Leu Val Thr Val Leu Glu Arg Tyr
545                 550                 555                 560

Gly Gln Val Phe Ser Lys Leu Cys Pro Asp Asn Asp Lys Gln Val Met
                565                 570                 575

Leu Leu Ser Gln Val Ser Thr Tyr Trp Lys Asn Asn Val Gln Met Thr
            580                 585                 590

Ala Val Ala Ile Asp Arg Met Met Gly Tyr Arg Leu Val Ser Asn Gln
        595                 600                 605

Ala Ile Val Arg Trp Val Phe Ser Pro Glu Asn Val Asp Gln Phe His
    610                 615                 620

Val Ser Asp Gln Pro Trp Glu Ile Leu Gly Asn Ala Leu Asn Lys Thr
625                 630                 635                 640

Tyr Asn Arg Ile Ser Asp Leu Arg Lys Asp Ile Ser Asn Ile Thr Lys
                645                 650                 655

Asn Val Leu Val Ala Glu Lys Ala Ser Ala Asn Ala Arg Val Glu Leu
                660                 665                 670

Glu Ala Ala Glu Ser Lys Leu Ser Leu Val Glu Gly Glu Pro Val Leu
            675                 680                 685

Gly Glu Asn Pro Ala Lys Met Lys Arg Leu Lys Ser Thr Val Glu Lys
        690                 695                 700

Thr Gly Glu Ala Glu Leu Ser Leu Arg Glu Ser Leu Glu Ala Lys Glu
705                 710                 715                 720

Ala Leu Leu Asn Arg Ala Leu Ser Glu Thr Glu Val Leu Leu Leu Leu
                725                 730                 735

Leu Phe Gln Ser Phe Leu Gly Val Leu Lys Glu Arg Leu Pro Asp Pro
                740                 745                 750

Thr Lys Val Arg Ser Val Gln Asp Leu Lys Ser Ile Gly Ala Glu Asp
            755                 760                 765

Asp Lys Pro Ser Ala Met Asp Val Asp Ser Glu Asn Gly Asn Pro Lys
        770                 775                 780

Lys Ser Cys Glu Val Gly Glu Arg Glu Gln Trp Cys Leu Ser Thr Leu
785                 790                 795                 800

Gly Tyr Leu Thr Ala Phe Thr Arg Gln Tyr Ala Ser Glu Ile Trp Pro
                805                 810                 815

His Met Glu Lys Leu Glu Ser Glu Val Phe Ser Gly Glu Asp Val His
                820                 825                 830

Pro Leu Phe Leu Gln Ala Ile Ser Ser Ala Leu Gln Phe Pro Leu His
            835                 840                 845
```

<210> SEQ ID NO 3
<211> LENGTH: 1250
<212> TYPE: DNA
<213> ORGANISM: Arabidopsis thaliana
<220> FEATURE:
<223> OTHER INFORMATION: genomic sequence containing promoter from ABH1 gene

<400> SEQUENCE: 3

```
gaaagggaaa ctcagccagc ctcggtaaaa acatcttctt ctgtttgcct ttctcttgta    60
atgatctcac atcatgtttg atggaatcta agactttgga tgggcatcta tttttatcat   120
gagttaatct tgacacaag  aaacatctct ttctaatctg ttcatagtca aaagaaattg   180
tgacaacttc accagatgga agttgtacct ctttattgtt acgaagtgga ttggcgacat   240
gaaacaaaac ccgaacacga acatagtcct gaaactgtga ttttcagag  tccatcacca   300
```

```
-continued cctccttcac ttccccaata cagctcgtga tctctttaat tgtgtcctga gtataatagt    360
tcaccgaaat attcctcact cgaccccaga ttggaagaaa attcagataa tcaattggag    420
gattctcaat ccatctatcc atgactacac cccaatttat cttctgtcca aactccaatt    480
ttcataattt cttctaaatc ttcctcagat ttgaagaaaa attggaatcg atcctttgag    540
agagcaacac ctctaacccg agaagaaatt ctccaaattc gtggcatatc taatatccaa    600
ttagacatcc tttgattctc tagattcaaa aacctaccca actaacgaca gttgtttctg    660
ttaattgaac aaaagcgcgg ttgatcagaa agaatcagag gcttattgtc ttaaatcgac    720
atattctgaa tggctttatc cagctccatg atgagatcct gatagagagt aaacaacttt    780
cccgaactcg tcaaacctga tttgcaggaa acaaactcca agagaaaaaa cagtgaagaa    840
atccgagtaa ttcagatgat aaccaacaca gaactgagaa tcacaaagca aactctcgta    900
acagagaaag agtcagaact accaaaaatc cgaggaagaa aacaacaatt tagaccggac    960
cgaacacgta aatatttctg gtagaagctc cgttcagaat agaacacctg agagaaaagt   1020
ctttaggctc caaattaact gggacgacta ttgttttaac ggctagtttc agctactaag   1080
agaaagaaga gagagaaaaa cttttttgtca aactcttttt gtgaactcct tttcttagat   1140
gacaacactt atgagaaaaa aaaaaaaaaa ttagtttga cgagacacgg acataaaaaa   1200
aaaaactagg gcagagtgac tgataccaaa ggagaaacaa caaagagacg              1250

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: RACE PCR
      plasmid rescue sequence internal primer

<400> SEQUENCE: 4
gaagctcaac tcgttgctgg aaag                                            24
```

MODULATION OF ABSCISIC ACID SIGNAL TRANSDUCTION IN PLANTS

CROSS-REFERENCES TO RELATED APPLICATIONS

This application is a continuation under 37 C.F.R. § 1.53(b) of U.S. Ser. No. 09/882,986, filed Jun. 14, 2001, now abandoned, which claims the benefit of U.S. Ser. No. 60/212,068, filed Jun. 14, 2000, the disclosures of which are incorporated herein by reference.

STATEMENT AS TO RIGHTS TO INVENTIONS MADE UNDER FEDERALLY SPONSORED RESEARCH AND DEVELOPMENT

This invention was made with Government support under Grant No. ROIGM60396-01, awarded by the National Institutes of Health and Grant No. MCB-9506191. The Government has certain rights in this invention.

BACKGROUND OF THE INVENTION

The present invention is directed to improving the ability to methods of modulating the action of the phytohormone abscisic acid (ABA) in plants. Modulating ABA activity in plants can be used, for example to confer drought tolerance on plants.

The phytohormone ABA regulates many agriculturally important stress and developmental responses throughout the life cycle of plants. In seeds, ABA is responsible for the acquisition of nutritive reserves, desiccation tolerance, maturation and dormancy (M. Koornneef et al., *Plant Physiol. Biochem.*, 36:83 (1998); J. Leung & J. Giraudat, *Annu. Rev. Plant. Physiol. Plant. Mol. Biol.*, 49:199 (1998)). During vegetative growth, ABA is a central internal signal that triggers plant responses to various adverse environmental conditions including drought, salt stress and cold (M. Koornneef et al., *Plant Physiol. Biochem.*, 36:83 (1998); J. Leung & J. Giraudat, *Annu. Rev. Plant. Physiol. Plant. Mol. Biol.*, 49:199 (1998)). A rapid response mediated by ABA is stomatal closure in response to drought (J. Leung & J. Giraudat, *Annu. Rev. Plant. Physiol. Plant. Mol. Biol.*, 49:199 (1998); E. A. C. MacRobbie, *Philos. Trans. R Soc. Lond. B Biol. Sci.*, 353:1475 (1998); J. M. Ward et al., *Plant Cell*, 7:833 (1995)). Stomata on the leaf surface are formed by pairs of guard cells whose turgor regulates stomatal pore apertures (E. A. C. MacRobbie, *Philos. Trans. R Soc. Lond. B Biol. Sci.*, 353:1475 (1998); J. M. Ward et al., *Plant Cell*, 7:833 (1995)). ABA induces stomatal closure by triggering cytosolic calcium ($[Ca^{2+}]_{cyt}$) increases which regulate ion channels in guard cells (E. A. C. MacRobbie, *Philos. Trans. R Soc. Lond. B Biol. Sci.*, 353:1475 (1998); J. M. Ward et al., *Plant Cell*, 7:833 (1995)). This response is vital for plants to limit transpirational water loss during periods of drought. Guard cells provide a well-suited system to characterize genes that affect early ABA signal transduction (F. Amstrong et al., *Proc. Natl. Acad. Sci. U.S.A.* 92:9520 (1995); Z.-M. Pei et al., *Plant Cell*, 9:409 (1997); J. Li et al., *Science*, 287:300 (2000)).

Two protein phosphatase mutations (abi1-1 and abi2-1) and a protein kinase mutant (aapk) that dominantly disrupt early events in ABA signaling (J. Leung & J. Giraudat, *Annu. Rev. Plant. Physiol. Plant. Mol. Biol.*, 49:199 (1998); F. Amstrong et al., *Proc. Natl. Acad. Sci. U.S.A.*, 92:9520 (1995); Z.-M. Pei et al., *Plant Cell*. 9:409 (1997); J. Li et al., *Science*, 287:300 (2000); K. Meyer et al., *Science*, 264:1452 (1994); J. Leung et al., *Science*, 264:1448 (1994)) and a recessive farnesyltransferase β subunit (era1-2) mutation that enhances early ABA signaling (S. Cutler et al., *Science*, 273:1239 (1996); Z.-M. Pei et al., *Science*, 282:287 (1998)) have been identified.

Identification of new ways of controlling ABA signal transduction would be desirable. Such methods would be particularly useful, for example, in controlling guard cell turgor and thus transpiration in plants. Such method would be particularly useful to limit transpirational water loss during periods of drought and thus render plants more drought tolerant. The present invention addresses these and other needs.

BRIEF SUMMARY OF THE INVENTION

The present invention provides methods of modulating ABA signal transduction in plants. In some embodiments, the methods are used to decreasing turgor pressure in guard cells and thereby render plants drought tolerant. The method comprise introducing into the plant a recombinant expression cassette comprising a promoter operably linked to an ABH1 polynucleotide that modulates ABA signal transduction in a plant. The ABH1 polynucleotides of the invention comprises a sequence at least about 70% identical to SEQ ID NO:1, or encode an ABH1 polypeptide having a sequence at least about 70% identical to SEQ ID NO:2.

In the methods of the invention the promoter used to drive expression of the ABH1 polynucleotide is typically a tissue-specific promoter. In many embodiments, it is a promoter that preferentially directs expression in guard cells, such as the KAT1 promoter.

The expression cassettes can be introduced into the plant using any of a number of well known techniques. These techniques include, for example, sexual crosses or *Agrobacterium*-mediated transformation.

The invention also provides isolated nucleic acid molecules comprising the ABH1 polynucleotides of the invention. In some embodiments, the nucleic acids will comprise an expression cassette, which will comprise a promoter operably linked to the ABH1 polynucleotide. In some embodiments, the tissue-specific promoter will preferentially direct expression in guard cells.

The invention further provides transgenic plant cells comprising an a recombinant expression cassette comprising a promoter operably linked to the ABH1 polynucleotides of the invention.

Definitions

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

The term "promote" refers to regions or sequence located upstream and/or downstream from the start of transcription and which are involved in recognition and binding of RNA polymerase and other proteins to initiate transcription. A "plant promoter" is a promoter capable of initiating transcription in plant cells.

The term "plant" includes whole plants, shoot vegetative organs and/or structures (e.g. leaves, stems and tubers), roots, flowers and floral organs (e.g. bracts, sepals, petals, stamens, carpels, anthers), ovules (including egg and central cells), seed (including zygote, embryo, endosperm, and seed coat), fruit (e.g., the mature ovary), seedlings, plant tissue (e.g. vascular tissue, ground tissue, and the like), cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety).

A polynucleotide "exogenous to" an individual plant is a polynucleotide which is introduced into the plant by any means other than by a sexual cross. Examples of means by which this can be accomplished are described below, and include *Agrobacterium*-mediated transformation, biolistic methods, electroporation, and the like. Such a plant containing the exogenous nucleic acid is referred to here as a T1 (e.g. in *Arabidopsis* by vacuum infiltration) or R0 (for plants regenerated from transformed cells in vitro) generation transgenic plant. Transgenic plants that arise from sexual cross or by selfing are descendants of such a plant.

An "ABH1 nucleic acid" or "ABH1 polynucleotide sequence" of the invention is a subsequence or full length polynucleotide sequence (SEQ ID NO:1) which, encodes an ABH1 polypeptide (SEQ ID NO:2) and its complement. ABH1 gene products of the invention (e.g., mRNAs or polypeptides) are characterized by the ability to modulate ABA signal transduction and thereby control such phenotypes as seed germination, stomatal closing, guard cell $[Ca^{2+}]_{cyt}$ elevations and whole plant transpirational water loss during drought. In addition, ABH1 polypeptides of the invention show homology to human and yeast nuclear RNA cap binding proteins named CBP80. An ABH1 polynucleotide of the invention typically comprises a coding sequence at least about 30–40 nucleotides to about 2500 nucleotides in length, usually less than about 3000 nucleotides in length. Usually the ABH1 nucleic acids of the invention are from about 100 to about 5000 nucleotides, often from about 500 to about 3000 nucleotides in length.

In the case of both expression of transgenes and inhibition of endogenous genes (e.g., by antisense, or co-suppression) one of skill will recognize that the inserted polynucleotide sequence need not be identical, but may be only "substantially identical" to a sequence of the gene from which it was derived. As explained below, these substantially identical variants are specifically covered by the term ABH1 nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "ABH1 nucleic acid", "ABH1 polynucleotide" and their equivalents. In addition, the terms specifically include those full length sequences substantially identical (determined as described below) with an ABH1 polynucleotide sequence and that encode proteins that retain the function of the ABH1 polypeptide (e.g., resulting from conservative substitutions of amino acids in the ABH1 polypeptide).

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11–17 (1988) e.g., as implemented in the program PC/GENE (Intelligenetics, Mountain View, Calif., USA).

The phrase "substantially identical," in the context of two nucleic acids or polypeptides, refers to a sequence or subsequence that has at least 25% sequence identity with a reference sequence. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 90%, 95%, or 99%, compared to a reference sequence using the programs described herein; preferably, BLAST using standard parameters, as described below. This definition also refers to the complement of a test sequence, when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESIFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., J. Mol. Biol. 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUIM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about 10–5, and most preferably less than about 10–20.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (13);
3) Asparagine (N), Glutamine (Q);
4) Arginine (R), Lysine (K);
5) Isoleucine (1), Leucine (L), Methionine (M), Valine (V); and
6) Phenylalanine (F), Tyrosine (Y), Tryptophan (W).
(see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, highly stringent conditions are selected to be about 5–10° C. lower than the thermal melting point (Tm) for the specific sequence at a defined ionic strength pH. Low stringency conditions are generally selected to be about 15–30° C. below the Tm. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising ABH1 nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

DETAILED DESCRIPTION OF THE INVENTION

The present invention is based at least in part on the characterization of a new recessive ABA hypersensitive *Arabidopsis* mutant, referred to here as abh1. Also described is the cloning and characterization of the gene responsible for this phenotype. The experiments described here indicate a novel functional link between a mRNA cap binding activity and modulation of early ABA signal transduction.

Results presented here indicate that ABH1 is a modulator of ABA signal transduction. ABH1 modulates the ABA sensitivity of seed germination, of ABA-induced stomatal closing, of ABA-induced guard cell $[Ca^{2+}]_{cyt}$ elevations and whole plant transpirational water loss during drought. Growth analyses with other plant hormones showed an ABA specificity of abh1. The abh1 mutant is the first plant mutant shown to enhance signal-induced $[Ca^{2+}]_{cyt}$ evations. Calcium imaging data demonstrate that ABH1 modulates early ABA signal transduction events. Human and yeast nuclear CBCs function in pre-mRNA splicing (E. Izaurralde et al., *Cell*, 78:657 (1994); J. D. Lewis et al., *Nucleic Acids Res.*, 24:3332 (1996)) and affect the expression of a specific subset of genes in yeast (P. Fortes et al., *Mol. Cell. Biol.*, 19:6543 (1999)). The nuclear CBC further regulates mRNA 3' end formation and RNA export in humans, and translation in yeast (E. Izaurralde et al., *Nature*, 376:709 (1995); P. Fortes et al., *Mol. Cell.*, 6:191 (2000)). Interestingly, the human nuclear CBC has recently been suggested to function as a target in growth factor and stress-activated signaling, regulating the expression of specific genes (K. F. Wilson et al., *J. Biol. Chem.*, 274:4 166 (1999)). The discovery of abh1 provides genetic evidence that a nuclear cap binding protein regulates ABA signaling in plants. Based on the mRNA cap binding activity ABH1 may regulate mRNA processing of early ABA signal transduction genes. Furthermore ABH1 modulates the strength of plant responses to ABA and therefore could provide a new control mechanism for manipulating the ABA responsiveness of crop plants during stress.

Increasing ABH1 Activity rABH1 Gene Expression

Any of a number of means well known in the art can be used to increase ABH1 activity in plants. Enhanced expression is useful for decreasing a plant's sensitivity to ABA. For example, enhanced expression can be used to control the development of abscission zones in leaf petioles and thereby control leaf loss.

Increasing ABH1 Gene Expression

Isolated sequences prepared as described herein can be used to introduce expression of a particular ABH1 nucleic acid to increase endogenous gene expression using methods well known to those of skill in the art. Preparation of suitable constructs and means for introducing them into plants are described below.

One of skill will recognize that the polypeptides encoded by the genes of the invention, like other proteins, have different domains that perform different functions. Thus, the gene sequences need not be full length, so long as the desired functional domain of the protein is expressed. The distinguishing features of ABH1 polypeptides are discussed below.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

Modification of Endogenous ABH1 Genes

Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used.

Alternatively, homologous recombination can be used to induce targeted gene modifications by specifically targeting the ABH1 gene in vivo (see, generally, Grewal and Klar, *Genetics*, 146:1221–1238 (1997) and Xu et al., *Genes Dev.*, 10:2411–2422 (1996)). Homologous recombination has been demonstrated in plants (Puchta et al., *Experientia* 50:277–284 (1994), Swoboda et al., *EMBO J.*, 13:484–489 (1994); Offringa et al., *Proc. Natl. Acad. Sci. USA*, 90:7346–7350 (1993); and Kempin et al. *Nature*, 389: 802–803 (1997)).

In applying homologous recombination technology to the genes of the invention, mutations in selected portions of an ABH1 gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA*, 91:4303–4307 (1994); and Vaulont et al., *Transgenic Res.*, 4:247–255 (1995) are conveniently used to increase the efficiency of selecting for altered ABH1 gene expression in transgenic plants. The mutated gene will interact with the target wild-type gene in such a way that homologous recombination and targeted replacement of the wild-type gene will occur in transgenic plant cells, resulting in modulation of ABH1 activity.

Alternatively, oligonucleotides composed of a contiguous stretch of RNA and DNA residues in a duplex conformation with double hairpin caps on the ends can be used. The RNA/DNA sequence is designed to align with the sequence of the target ABH1 gene and to contain the desired nucleotide change. Introduction of the chimeric oligonucleotide on an extrachromosomal T-DNA plasmid results in efficient and specific ABH1 gene conversion directed by chimeric molecules in a small number of transformed plant cells. This method is described in Cole-Strauss et al., *Science*, 273: 1386–1389 (1996) and Yoon et al. *Proc. Natl. Acad. Sci. USA*, 93:2071–2076 (1996).

Other Means for Increasing ABH1 Activity

One method to increase ABH1 expression is to use "activation mutagenesis" (see, e.g. Hiyashi et al. *Science*, 258:1350–1353 (1992)). In this method an endogenous ABH1 gene can be modified to be expressed constitutively, ectopically, or excessively by insertion of T-DNA sequences that contain strong/constitutive promoters upstream of the endogenous ABH1 gene. As explained below, preparation of transgenic plants overexpressing ABH1 can also be used to increase ABH1 expression. Activation mutagenesis of the endogenous ABH1 gene will give the same effect as overexpression of the transgenic ABH1 nucleic acid in transgenic plants. Alternatively, an endogenous gene encoding an enhancer of ABH1 activity or expression of the endogenous ABH1 gene can be modified to be expressed by insertion of T-DNA sequences in a similar manner and ABH1 activity can be increased.

Another strategy to increase ABH1 expression can be the use of dominant hyperactive mutants of ABH1 by expressing modified ABH1 transgenes. For example expression of modified ABH1 with a defective domain that is important for interaction with a negative regulator of ABH1 activity can be used to generate dominant hyperactive ABH1 proteins. Alternatively, expression of truncated ABH1 proteins which have only a domain that interacts with a negative regulator can titrate the negative regulator and thereby increase endogenous ABH1 activity. Use of dominant mutants to hyperactivate target genes is described in Mizukami et al, *Plant Cell*, 8:831–845 (1996).

Inhibition of ABH1 Activity or Gene Expression

As explained above, ABH1 activity is important in controlling ABA signal transduction. In some embodiments, expression of ABH1 in guard cell is controlled, thereby controlling stomatal opening. Inhibition of ABH1 gene expression activity can be used, for instance, to increase drought tolerance by decreasing transpiration in transgenic plants. Targeted expression of ABH1 nucleic acids that inhibit endogenous gene expression (e.g., antisense or cosuppression) can be used for this purpose.

Inhibition of ABH1 Gene Expression

The nucleic acid sequences disclosed here can be used to design nucleic acids useful in a number of methods to inhibit ABH1 or related gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci.* (*Limerick*) 105:125–149 (1995); Pantopoulos In *Progress in Nucleic Acid Research and Molecular Biology*, Vol. 48. Cohn, W. E. and K. Moldave (Ed.). Academic Press, Inc.: San Diego, Calif., USA; London, England, UK. p. 181–238; Heiser et al *Plant Sci.*, (Shannon) 127:61–69 (1997)) and by preventing the accumulation of mRNA which encodes the protein of interest, (see, Baulcombe, *Plant Mol Bio.*, 32:79–88 (1996); Prins and Goldbach, *Arch. Virol.*, 141:2259–2276 (1996); Metzlaff et al *Cell*, 88 845–854 (1997), Sheehy et al., *Proc. Nat. Acad. Sci. USA*, 85:8805–8809 (1988), and Hiatt et al., U.S. Pat. No. 4,801, 340).

The nucleic acid segment to be introduced generally will be substantially identical to at least a portion of the endogenous ABH1 gene or genes to be repressed. The sequence, however, need not be perfectly identical to inhibit expression. The vectors of the present invention can be designed such that the inhibitory effect applies to other genes within a family of genes exhibiting identity or substantial identity to the target gene.

For antisense suppression, the introduced sequence also need not be full length relative to either the primary transcription product or fully processed mRNA. Generally, higher identity can be used to compensate for the use of a shorter sequence. Furthermore, the introduced sequence need not have the same intron or exon pattern, and identity of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 3500 nucleotides is especially preferred.

A number of gene regions can be targeted to suppress ABH1 gene expression. The targets can include, for instance, the coding regions, introns, sequences from exon/intron junctions, 5' or 3' untranslated regions, and the like.

Another well known method of suppression is sense co-suppression. Introduction of nucleic acid configured in the sense orientation has been recently shown to be an effective means by which to block the transcription of target genes. For an example of the use of this method to modulate expression of endogenous genes (see, Assaad et al. *Plant Mol. Bio.*, 22:1067–1085 (1993); Flavell, *Proc. Natl. Acad. Sci. USA*, 91:3490–3496 (1994); Stam et al. *Annals Bot.*, 79:3–12 (1997); Napoli et al., *The Plant Cell*, 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting identity or substantial identity.

For co-suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using co-suppression technologies.

Oligonucleotide-based triple-helix formation can also be used to disrupt ABH1 gene expression. Triplex DNA can inhibit DNA transcription and replication, generate site-specific mutations, cleave DNA, and induce homologous recombination (see, e.g., Havre and Glazer, *J. Virology*, 67:7324–7331 (1993); Scanlon et al., *FASEB J.*, 9:1288–1296 (1995); Giovannangeli et al., *Biochemistry*, 35:10539–10548 (1996); Chan and Glazer, *J. Mol. Medicine (Berlin)*, 75:267–282 (1997)). Triple helix DNAs can be used to target the same sequences identified for antisense regulation.

Catalytic RNA molecules or ribozymes can also be used to inhibit expression of ABH1 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, luceme transient streak virus, velvet tobacco mottle virus, solanum nodiflorum mottle virus and subterranean clover mottle virus. The design and use of target RNA-specific ribozymes is described in Zhao and Pick, *Nature*, 365:448–451 (1993); Eastham and Ahlering, *J. Urology*, 156:1186–1188 (1996); Sokoi and Murray, *Transgenic Res.*, 5:363–371 (1996); Sun et al., *Mol. Biotechnology*, 7:241–251 (1997); and Haseloff et al., *Nature*, 334:585–591 (1988).

Modification of Endogenous ABH1 Genes

Methods for introducing genetic mutations described above can also be used to select for plants with decreased ABH1 expression.

ABH1 activity may be modulated by eliminating the proteins that are required for ABH1 cell-specific gene expression. Thus, expression of regulatory proteins and/or the sequences that control ABH1 gene expression can be modulated using the methods described here.

Another strategy is to inhibit the ability of an ABH1 protein to interact with itself or with other proteins. This can be achieved, for instance, using antibodies specific to ABH1. In this method cell-specific expression of ABH1-specific antibodies is used to inactivate functional domains through antibody:antigen recognition (see, Hupp et al, *Cell*, 83:237–245 (1995)). Interference of activity of an ABH1 interacting protein(s) can be applied in a similar fashion. Alternatively, dominant negative mutants of ABH1 can be prepared by expressing a transgene that encodes a truncated ABH1 protein. Use of dominant negative mutants to inactivate target genes in transgenic plants is described in Mizukami et al., *Plant Cell*, 8:831–845 (1996).

Isolation of ABH1 Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989) or *Current Protocols in Molecular Biology*, Volumes 1–3, John Wiley & Sons, Inc. (1994–1998).

Using the sequences provided here, the isolation of ABH1 nucleic acids the sequence provided here may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as flowers, and a cDNA library which contains the ABH1 gene transcript is prepared from the mRNA. Alternatively, cDNA may be prepared from mRNA extracted from other tissues in which ABH1 genes or homologs are expressed.

The cDNA or genomic library can then be screened using a probe based upon the sequence of a cloned ABH1 gene disclosed here. Probes may be used to hybridize with genomic DNA or cDNA sequences to isolate homologous genes in the same or different plant species. Alternatively, antibodies raised against an ABH1 polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the ABH1 genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: A Guide to Methods and Applications. (Innis, M, Gelfand, D., Sninsky, J. and White, T., eds.), Academic Press, San Diego (1990).

Polynucleotides may also be synthesized by well-known techniques as described in the technical literature. See, e.g., Carruthers et al., *Cold Spring Harbor Symp. Quant. Biol.*, 47:411–418 (1982), and Adams et al., *J. Am. Chem. Soc.*, 105:661 (1983). Double stranded DNA fragments may then be obtained either by synthesizing the complementary strand and annealing the strands together under appropriate conditions, or by adding the complementary strand using DNA polymerase with an appropriate primer sequence.

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.*, 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill. Such genes include for example, ACT11 from *Arabidopsis* (Huang et al. *Plant Mol. Biol.*, 33:125–139 (1996)), Cat3 from *Arabidopsis* (GenBank No. U43147, Zhong et al., *Mol. Gen. Genet.*, 251:196–203 (1996)), the gene encoding stearoyl-acyl carrier protein desaturase from *Brassica napus* (Genbank No. X74782, Solocombe et al. *Plant Physiol.*, 104:1167–1176 (1994)), GPc1 from maize (GenBank No. X15596, Martinez et al. *J. Mol. Biol*, 208:551–565 (1989)), and Gpc2 from maize (GenBank No. U45855, Manjunath et al., *Plant Mol. Biol.*, 33:97–112 (1997)).

Alternatively, the plant promoter may direct expression of the ABH1 nucleic acid in a specific tissue, organ or cell type (i.e. tissue-specific promoters) or may be otherwise under more precise environmental or developmental control (i.e. inducible promoters). Examples of environmental conditions that may effect transcription by inducible promoters include anaerobic conditions, elevated temperature, the presence of light, or sprayed with chemicals/hormones. One of skill will recognize that a tissue-specific promoter may drive expression of operably linked sequences in tissues other than the target tissue. Thus, as used herein a tissue-specific promoter is one that drives expression preferentially in the target tissue or cell type, but may also lead to some expression in other tissues as well.

A number of tissue-specific promoters can also be used in the invention. For instance, promoters that direct expression of nucleic acids in guard cells are useful for conferring drought tolerance. One such particularly preferred promoter is KAT1, which has been shown in transgenic plants to drive expression primarily in guard cells (see, Nakamura, R., et al., *Plant Physiol.*, 109:371–374 (1995). Another particularly preferred promoter is the truncated 0.3 kb 5' proximal fragment of potato ADP-glucose pyrophosphorylase, which has been shown to drive expression exclusively in guard cells of transgenic plants. See, e.g., Muller-Rober, B., et al., *Plant Cell*, 6:601–612 (1994).

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, (G418, bleomycin, hygromycin, or herbicide resistance, such as resistance to chlorosulfuron or Basta.

The present invention also provides promoter sequences from the ABH1 gene (SEQ ID NO: 3), which can be used to direct expression of the ABH1 coding sequence or heterologous sequences in desired tissues.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J.*, 3:2717–2722 (1984). Electroporation techniques are described in Fromm et al. *Proc. Natl. Acad. Sci. USA*, 82:5824 (1985). Ballistic transformation techniques are described in Klein et al. *Nature*, 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria *Agrobacterium tumefaciens*-mediated transformation techniques, including disarming and use of binary vectors, are well described in the scientific literature. See, for example Horsch et al. *Science*, 233:496–498 (1984), and Fraley et al. *Proc. Natl. Acad. Sci. USA*, 80:4803 (1983) and Gene Transfer to Plants, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as decreased farnesyltransferase activity. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al, *Ann. Rev, of Plant Phys.*, 38:467–486 (1987).

The nucleic acids of the invention can be used to confer desired traits on essentially any plant. Thus, the invention has use over a broad range of plants, including species from the genera *Anacardium, Arachis, Asparagus, Atropa, Avena, Brassica, Chlamydomonas, Chlorella, Citrus, Citrullus, Capsicum, Carthamus, Cocos, Coffea, Cucumis, Cucurbita, Cyrtomium, Daucus, Elaeis, Fragaria, Glycine, Gossypium, Helianthus, Heterocallis, Hordeum, Hyoscyamus, Lactuca, Laminaria, Linum, Lolium, Lupinus, Lycopersicon, Macrocystis, Malus, Manihot, Majorana, Medicago, Nereocystis, Nicotiana, Olea, Oryza, Osmunda, Panieum, Pannesetum, Persea, Phaseolus, Pistachia, Pisum, Pyrus, Polypodium, Prunus, Pteridium, Raphanus, Ricinus, Secale, Senecio, Sinapis, Solanum, Sorghum, Theobromus, Trigonelia, Triticum, Vicia, Vitis, Vigna*, and *Zea*. In particular, the invention is useful with any plant with guard cells.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of ABH1 mRNA or protein in transgenic plants. Means for detecting and quantitating mRNAs or proteins are well known in the art. The plants of the invention can also be identified by detecting the desired phenotype. For instance, measuring cytosolic calcium levels in guard cells, stomatal aperatures, seed germination in the presence of ABA, drought tolerance, using methods as described below.

The following Examples are offered by way of illustration, not limitation.

EXAMPLES

The abh1 mutant was isolated from 3,000 activation-tagged *Arabidopsis thaliana* lines because its germination was inhibited by 0.3 μM ABA, a concentration that allowed germination of wild-type seeds. This was carried out using *Arabidopsis* lines (Columbia background, T3 seeds), which were transformed with a T-DNA (SK1015) (D. Weigel et al., *Plant Physiol.*, 122:1003 (2000)), and plated on minimum medium (0.25×MS) with 0.3 μM ABA. After 4 days at 4° C., seeds were transferred to 28° C., continuous light. After 5 more days, germination was analyzed. Non-germinated seeds were transferred to soil and further analyzed. In the absence of exogenous ABA, abh1 seeds showed wild-type germination rates after pre-exposure to 4° C. for 4 days. Pre-exposure to 4° C. for only two days showed slightly enhanced dormancy of abh1.

Genetic and Southern blot analyses showed that the abh1 mutation was recessive and segregated as a single nuclear locus linked to the resistance marker ($\chi^2$=0.50, P>0.47), suggesting that abh1 is a loss-of-function mutation. The ABA contents (S. H. Schwartz et al., *Plant Physiol*, 114:161 (1997)) of wild-type and abh1 plants were similar suggesting that ABH1 affects ABA sensitivity rather than biosynthesis (0.18 and 0.16 μg/g ABA in seeds, and 0.14 and 0.12 μg/g dry weight in vegetative tissues for wild-type and abh1, respectively.

To determine whether the abh1 mutation was specific to ABA signaling, seed germination, hypocotyl and root growth assays were performed in the presence of ABA, cytokinin, brassinosteroid, auxin, ethylene (using the precursor 1-aminocyclopropane-1-carboxylic acid), methyl jasmohate (JA) and gibberellic acid (GA) at hormone concentrations from 10 nM to 100 μ.M. The abh1 mutant showed phenotypic responses only to ABA and a slightly reduced sensitivity to GA which was not surprising, as GA is antagonistic to ABA. Other hormone signaling mutants were analyzed in control experiments: axr1–3 (auxin insensitive) (C. Lincoln et al., *Plant Cell*, 2:1071(1990)), ein2-1 (ethylene insensitive) (J. M. Alonso et al., *Science*, 284:2148 (1999)), gai-1 (GA insensitive) (M. Koornneef et al., *Physiol Plant.*, 65:33 (1985)), era1-2 (ABA hypersensitive) (S. Cutler et al., *Science*, 273:1239 (1996))), and jar1-1 (JA insensitive) (P. E. Staswick et al., *Proc. Natl. Acad. Sci. U.S.A.*, 89:6837 (1992)). Interestingly all of these mutants exhibited significantly altered responses to more than one of the exogenously added hormones suggesting cross-talk or feedback interactions of these loci with multiple signaling pathways. These data further highlight the ABA specificity of abh1 relative to other hormones.

ABH1 is expressed in guard cells. To determine whether ABH1 modulates early ABA signal transduction elements, stomatal closure in response to ABA was investigated. Stomata were opened by exposing plants for 12 hours to high humidity (95%). Under these conditions stomatal apertures were similar in wild-type and abh1 (2.03±0.19 μm, wild-type, n=60; 1.92±0.21 μm, abh1, n=60; P>0.38). Stomatal closure in abh1 was ABA hypersensitive compared to wild-type (P<0.001). When stomatal apertures were measured in leaves harvested directly from plants grown under lower humidity (40%), without exogenous ABA addition, stomatal apertures of abh1 were smaller than those of wild-type plants (P<0.001), possibly resulting from a hypersensitive response to endogenous ABA.

Stomatal closing in response to ABA includes activation of guard cell slow anion channels and inhibition of inward-rectifying $K^+$ channels (F. Amstrong et al., *Proc. Natl. Acad. Sci. U.S.A.*, 92:9520 (1995); Z.-M. Pei et al, *Plant Cell*, 9:409 (1997); J. Li et al., *Science*, 287:300 (2000), Z.-M. Pei et al., *Science*, 282:287 (1998)). Patch clamp experiments without addition of ABA showed that in abh1 guard cells from 40% humidity grown plants, anion currents were consistently larger than those in wild-type guard cells (abh1: n=35, wild-type: n=26, P<0.001); whereas inward-rectifying K⁺ channel currents were substantially smaller in abh1 guard cells (abh1 n=14, wild-type n=13, P<0.001) (Y. Murata et al, unpublished data.). These data correlated well with stomatal apertures in 40% humidity grown plants. Furthermore, in the presence of exogenous ABA, anion currents were larger in abh1 guard cells (n=15) than in wild-type guard cells (n=17) (p<0.05).

Due to the basal regulation of anion and K⁺ channels in abh1 without addition of exogenous ABA, experiments were pursued to analyze whether mechanisms lying further upstream confer ABA hypersensitivity in abh1. Anion channels are activated and inward-rectifying K⁺ channels are down-regulated by upstream $[Ca^{2+}]_{cyt}$ elevations (J. I. Schroeder & S. Hagiwara, Nature, 338:427 (1989)). Therefore we directly investigated whether abh1 modulates ABA-induced $[Ca^{2+}]_{cyt}$ elevations in time-resolved cameleon $[Ca^{2+}]_{cyt}$ imaging experiments (G. J. Allen et al, The Plant J., 19:735 (1999)). Stomata were opened by exposing plants for 12 hours to 95% humidity. In wild-type, 56% (n=32 of 57) of guard cells showed no $[Ca^{2+}]_{cyt}$ increase in response to a low concentration of 0.5 μM ABA and the remaining 44% (n=25) cells typically showed only one $[Ca^{2+}]_{cyt}$ increase with an average peak increase of 170±25 nM $[Ca^{2+}]_{cyt}$. Interestingly, in abh1 guard cells, 0.5 μM ABA elicited $[Ca^{2+}]_{cyt}$ increases in 64% of guard cells (n=41 of 64 cells) with a larger average peak increase of 280±22 μM Only 19% of the cells (n=12) responded with one $[Ca^{2+}]_{cyt}$ elevation while 45% of abh1 cells (n=29) showed multiple repetitive $[Ca^{2+}]_{cyt}$ increases at 0.5 μM ABA. Only 36% of abh1 cells (n=23) showed no response to 0.5 μM ABA. Statistical analyses of responsive versus non-responsive cells confirmed that the ABA responsiveness of abh1 guard cells was significantly enhanced ($\chi^2$=4.96, P<0.03). Furthermore both the number of $[Ca^{2+}]_{cyt}$ transients per cell (P<0.001) and their amplitudes (P<0.01) were significantly larger in abh1 than in wild-type. $[Ca^{2+}]_{cyt}$ imaging analyses and stomatal aperture measurements demonstrate that the abh1 mutation enhances early ABA-signaling mechanisms upstream of ABA-induced $[Ca^{2+}]_{cyt}$ elevation.

The abh1 mutant showed slightly slowed growth and moderately serrated leaves. No other visible whole plant phenotypes were observed. When plants were subjected to water stress, ABA content (S. H. Schwartz et al., Plant Physiol., 114:161(1997)) increased to similar levels in wild-type and abh1 (1.33 and 1.26 μg/g of dry weight (experiment 1) and 1.05 and 1.26 μg/g (experiment 2) in wild-type and abh1 respectively). After 3 weeks without watering, (40% growth chamber humidity), abh1 rosette and cauline leaves remained green and turgid whereas wild-type leaves showed chlorosis and wilting (n=40 abh1, n=40 wild-type plants, in two independent experiments). After 10 days of drought, abh1 plants already showed stomatal closing compared to control watered (P<0.01); whereas wild-type plants did not (P>0.5) (10 days drought, stomatal apertures: 1.14±0.04 μm in abh1, n=60; 1.41±0.07 μm in wild-type, n=60; watered controls: 1.25±0.08 μm in abh1, n=60; 1.42±0.05 μm in wild-type, n=60). Together these results suggest that ABA hypersensitive stomatal closing contributes to reduced desiccation and wilting of abh1 leaves.

The ABH1 gene was identified by plasmid rescue and the corresponding cDNA (2547 bp) was isolated. Briefly, a 278 bp genomic fragment adjacent to the right border of the T-DNA insertion was isolated from abh1 plants using plasmid rescue as follows: 5 μg of genomic DNA was digested with HindIII, self-ligated and transformed into E. coli ElectroMAX DH12S (GibcoBRL, Lifetechnology). Plasmid extracted from cells growing on carbenicilin was sequenced. Primers were then generated to amplify 5316 bp genomic DNA flanking the rescued sequence (GenomeWlkaer Kit, Clontech). A 8248 bp ClaI genomic fragment containing the full ABH1 locus was cloned from BAC T10F2 (Arabidopsis Biological Research Center) into the plant expression vector pRD400. ABH1 coding sequences were amplified from an Arabidopsis Columbia leaf cDNA library by rapid amplification of cDNA ends (RACE PCR, Marathon cDNA Amplification Kit, Clontech) using the plasmid rescue sequence internal primer (5' GAAGCTCAACTCGTTGCTGGAAAG 3'; SEQ. ID NO:4) and its reverse. The total cDNA of 2547 bp was then amplified using pfu DNA polymerase (Stratagene), cloned in pMON530 and sequenced. ABH1 5' UTR (1250 bp) was amplified from genomic DNA by PCR using pfu DNA polymerase and subcloned in pCAMBIA1303 (Genbank AF23299) containing a promoterless glucuronidase reporter gene. All sequences amplified by PCR were checked by sequencing (Retrogen, CA).

The ABH1 gene is located on chromosome II and consists of 18 exons. ABH1 is a single gene in the Arabidopsis genome (SEQ ID NO:1). The T-DNA in abh1 was inserted at the end of the $8^{th}$ intron. Northern blot analyses showed that ABH1 transcript was absent in abh1 but present in wild-type leaves. Northern blot analysis further showed ABH1 expression in roots, leaves, stems and flowers.

The abh1 plants were transformed with the ABH1 gene under the control of its own promoter and with the ABH1 cDNA under the control of the CaMV 35S promoter. Agrobacterium tumefaciens strain C58 was used to generate Arabidopsis transgenic seedlings using the floral dipping method (S. J. Clough and A. F. Bent, Plant J., 16:735 (1998)). Seeds from homozygous abh1 plants transformed with either construct showed wild-type germination rates in the presence of 0.3 μm ABA, illustrating abh1 complementation. Stomatal apertures of abh1 plants transformed with the ABH1 genomic construct and grown at 40% humidity were comparable to apertures of wild-type plants and significantly larger than abh1 apertures (P<0.001; n=60, 3 independent complemented lines with ABH1 gene). Furthermore the stomatal ABA sensitivity of complemented plants grown for 12 hours at 95% humidity was similar to that of wild-type (n=60, 2 complemented lines, P>0.32). Furthermore, $K^+_{in}$ currents (n=6) and anion currents (n=6) showed wild-type magnitudes in a complemented line transformed with the ABH1 gene and grown at 40% humidity (P>0.7 and P>0.13, respectively).

ABH1 encodes a large protein of 850 amino acids with significant similarity to a specific class of human and yeast nuclear RNA cap binding proteins named CBP80 which thus far have not been described in plants. ABH1 shares 33.8% and 45% similarity with the yeast (P34160) and human (NP_002477) CBP80, respectively. In humans and yeast CBP80 is a subunit of a heterodimeric nuclear cap binding complex (CBC), together with CBP20 (E. Izaurralde et al., Cell, 78:657 (1994); E. Izaurralde et al., Nature, 376:709 (1995); J. D. Lewis et al., Nucleic Acids Res., 24:3332 (1996)). The nuclear CBCs play important roles in mRNA processing and in nerve growth factor and stress-activated signal transduction pathways (E. Izaurralde et al., Cell, 78:657 (1994); E. Izaurralde et al., Nature, 376:709 (1995); J. D. Lewis et al., Nucleic Acids Res., 24:3332 (1996); N. Kataoka et al., Nucleic Acids Res., 23:3638 (1995); P. Fortes et al., Mol. Cell. Biol., 19:6543 (1999); K. F. Wilson et al., J. Biol. Chem., 274:4166 (1999)). An Arabidopsis CBP20 homolog (AtCBP20) was identified on chromosome V (AAD29697). Yeast two-hybrid experiments showed interaction between ABH1 and AtCBP20, indicating that ABH1 may be a subunit of an *Arabidopsis* nuclear CBC. Nuclear CBCs bind to the monomethylated (m⁷ GpppN) cap structure of RNA transcribed by RNA polymerase II (E. Izurralde et al., *Cell*, 78:657 (1994); N. Kataoka et al., *Nucleic Acids Res.*, 23:3638 (1995); K. F. Wilson et al., *J. Biol. Chem.*, 274:4166 (1999)). Whole cell extracts from yeast cells expressing both ABH1 and AtCBP20 subunits showed mRNA cap binding activity. This cap binding activity was not detectable in control wild-type yeast strain extracts or when only one of the two CBC subunits were expressed alone, showing that this activity requires the presence of both ABH1 and AtCBP20. Moreover, the cap binding activity was abolished when monomethylated cap structure was added as a competitor, but not when an ApppN cap analogue was added. No binding activity was observed when an A-primed RNA was used as RNA probe. These results strongly suggest that ABH1 functions as a subunit of an *Arabidopsis* CBC.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method for enhancing sensitivity to abscisic acid in a plant, comprising:
introducing into the plant a nucleic acid molecule that comprises an ABH1 polynucleotide sequence operably linked in the antisense orientation to a plant promoter, wherein the ABH1 polynucleotide sequence is SEQ ID NO:1, and is expressed so as to inhibit the expression of ABH1 protein in said plant and to enhance drought tolerance of said plant.

2. The method of claim 1, wherein the promoter is a tissue-specific promoter.

3. The method of claim 2, wherein the tissue-specific promoter preferentially directs transcription in guard cells.

4. The method of claim 3, wherein the tissue-specific promoter is a KAT1 promoter.

5. The method of claim 1, wherein the nucleic acid is introduced into the plant using *Agrobacterium*.

6. The method of claim 1, wherein the nucleic acid is introduced into the plant by electroporation.

7. The method of claim 1, wherein the nucleic acid is introduced into the plant by DNA particle bombardment.

8. The method of claim 1, wherein the nucleic acid is introduced into the plant by sexual cross.

9. A transgenic plant with enhanced sensitivity to abscisic acid, the transgenic plant comprising an ABH1 polynucleotide sequence operably linked in the antisense orientation to a plant promoter, wherein the ABH1 polynucleotide sequence is SEQ ID NO:1, and is expressed so as to inhibit the expression of ABH1 protein in said plant and to enhance drought tolerance of said plant.

10. The transgenic plant of claim 9, wherein the promoter is a tissue-specific promoter.

11. The transgenic plant of claim 10, wherein the tissue-specific promoter preferentially directs transcription in guard cells.

12. The nucleic acid of claim 11, wherein the tissue-specific promoter is a KAT1 promoter.

13. The transgenic plant of claim 9, wherein the nucleic acid is introduced into the plant cell through sexual cross.

14. The transgenic plant of claim 9, wherein the nucleic acid is introduced into the plant cell using *Agrobacterium*.

15. The transgenic plant of claim 9 wherein the nucleic acid is introduced into the plant cell using electroporation.

16. The transgenic plant of claim 9 wherein the nucleic acid is introduced into the plant using DNA particle bombardment.

* * * * *

UNITED STATES PATENT AND TRADEMARK OFFICE
CERTIFICATE OF CORRECTION

PATENT NO. : 7,199,285 B2
APPLICATION NO. : 10/740084
DATED : April 3, 2007
INVENTOR(S) : Schroeder et al.

Page 1 of 1

It is certified that error appears in the above-identified patent and that said Letters Patent is hereby corrected as shown below:

Title page Item (56), under "Other Publications", in column 2, line 30, delete "Farneyltransferase" and insert -- Farnesyltransferase --, therefor.

Signed and Sealed this

First Day of July, 2008

JON W. DUDAS
*Director of the United States Patent and Trademark Office*